US005620608A

United States Patent [19]

Rosa et al.

[11] Patent Number: 5,620,608
[45] Date of Patent: Apr. 15, 1997

[54] INFORMATION ENTRY VALIDATION SYSTEM AND METHOD FOR A DIALYSIS MACHINE

[75] Inventors: Jim Rosa, Conifer; Eric Zimmerman, Littleton; Steve Love, Bailey; Scott Martin, Lakewood, all of Colo.

[73] Assignee: COBE Laboratories, Inc., Lakewood, Colo.

[21] Appl. No.: 484,015

[22] Filed: Jun. 7, 1995

[51] Int. Cl.⁶ .................................................. B01D 61/32
[52] U.S. Cl. .................. 210/739; 210/143; 210/646; 604/4; 395/167; 395/326; 395/356
[58] Field of Search .......................... 210/85, 143, 646, 210/929, 94, 745, 739; 604/4–6; 364/413.01, 413.02, 413.07; 395/140, 150, 155, 160, 161, 924, 156

[56] References Cited

U.S. PATENT DOCUMENTS

| | | | |
|---|---|---|---|
| 4,370,983 | 2/1983 | Lichtenstein | 210/929 |
| 4,725,694 | 2/1988 | Auer et al. | 178/18 |
| 4,756,706 | 7/1988 | Kerns et al. | 604/66 |
| 4,796,634 | 1/1989 | Huntsman et al. | 128/662.01 |
| 4,990,258 | 2/1991 | Bjare et al. | 210/647 |
| 5,053,684 | 10/1991 | Nooyen | 315/392 |
| 5,189,609 | 2/1993 | Tivig et al. | |
| 5,276,611 | 1/1994 | Ghiraldi | |
| 5,319,363 | 6/1994 | Welch et al. | 340/825.36 |
| 5,326,476 | 7/1994 | Grogan et al. | 210/646 |
| 5,472,614 | 12/1995 | Rossi | 210/646 |

FOREIGN PATENT DOCUMENTS

0432138A2  6/1991  European Pat. Off. .

*Primary Examiner*—Joseph W. Drodge
*Attorney, Agent, or Firm*—John R. Ley

[57] ABSTRACT

Information is entered and validated by the operator of a dialysis machine by converting the entered information into a first form using a first conversion relationship such as ASCII. The information in the first form is next converted into a second form using a second conversion relationship, such as floating point numeric. Thereafter the information in the second form is converted back to the first form using the first conversion relationship. The information in the first form which resulted from the third conversion is displayed for acceptance for rejection by the operator. The multiple sequential conversions indicate the proper functionality of a safety system of the dialysis machine. Displaying the information resulting from sequential multiple conversions assures an opportunity for the operator to evaluate the entries for accuracy. Re-display of the previously entered information repeatedly presents the operator with an opportunity to recognize human-induced errors.

44 Claims, 12 Drawing Sheets

INFORMATION ENTRY VALIDATION SYSTEM AND METHOD FOR A DIALYSIS MACHINE

The present invention relates to a new and improved dialysis machine and method of validating information entered by a machine operator to control the machine during dialysis treatment. More particularly, the present invention effectively confirms that the entered information is what the operator intended and that the machine validly accepted the information, all of which occurs more conveniently for the operator while maintaining safety according to commonly accepted safety standards.

CROSS REFERENCE TO RELATED INVENTIONS

This invention is related to the inventions described in U.S. patent applications for a Graphical Operator Machine Interface and Method for Information Entry and Selection in a Dialysis Machine, Ser. No. 08/486,944 and for a Single Microcontroller Execution of Control and Safety System Functions in a Dialysis Machine, Ser. No. 08/438,456, both of which were filed concurrently herewith. The disclosures of these applications are incorporated herein by this reference.

BACKGROUND OF THE INVENTION

In general, a dialysis machine is used as a substitute for the natural kidney functions of a human body. As such, the dialysis machine cleanses the blood of the natural accumulation of bodily wastes and separates the wastes from the blood outside of or extracorporeally of the body. The separated wastes are discharged, and the cleansed blood is returned to the body.

The wastes are separated from the blood in a dialyzer. The dialyzer includes an internal housing which is separated by a porous medium into a blood side or compartment and a dialysate side or compartment. The blood removed from the patient flows through the blood side of the dialyzer. A prepared solution of dialysate is passed through the dialysate side of the dialyzer. The wastes from the blood pass through the medium by osmosis, ionic transfer or fluid transport into the dialysate and, depending upon the type of dialysis treatment, desirable components from the dialysate may pass in the opposite direction through the medium and into the blood. The transfer of the wastes into the dialysate cleanses the blood while allowing the desired components from the dialysate to enter the bloodstream.

As is apparent, the dialysis machine must be properly operated to perform effective dialysis in a safe and reliable manner. With the blood of the patient being removed and handled outside of the patient's body in an extracorporeal flow path, care must be taken that the treatment progresses safely and as intended according to the dialysis prescription for the patient. Since the patient's blood and the dialysate separated only by the dialyzer medium, it is apparent that numerous safety concerns must be satisfied on a continual and reliable basis.

Because of the potential for extremely serious consequences resulting from a failure or other unsafe condition, modern dialysis machines incorporate a large number of safety features as well as extensive control system features. The safety features include sensors located in the extracorporeal and dialysate flow paths to derive signals representative of the operating conditions or parameters which indicate the proper operation of the dialysis machine and/or the early development of a safety or risk condition. The control system features result in operational control over the pumas, dialysate heater, flow control valves and other devices associated with the extracorporeal and dialysate flow paths.

Because of the pre-eminent importance of the safety system, all known modern dialysis machines utilize microcontrollers or similar types of processor devices to execute the safety functions. Generally speaking, modern microcontrollers offer a greater possibility of more effective control over the safety features than other types of safety systems. Typically one microcontroller is used to execute the safety functions, and at least one and frequently two other microcontrollers execute the control system functions. Upon recognizing a safety or risk condition, the safety microcontroller takes control of the dialysis machine and places it in a safe state which prevents or greatly reduces the risk of injury to the patient.

In large measure, the use of separate microcontrollers for the safety and control systems is a result of the relatively stringent standards established by governmental, health and safety groups pertaining to dialysis machines. The multiple-microcontroller approach to achieving the basic safety and control system functions satisfies the regulatory standards by making the functionality of the safety system microcontroller independent of and separate from the functionality of the control system microcontroller.

The safety standards also apply to the entry of the information when setting up the machine to perform the dialysis treatment, as well as to the entry of information during the progress of the treatment. In general, the safety standards are concerned with promoting operator accuracy when entering information, and assuring that the entered information is not corrupted before it is used by the control system and safety system microcontrollers.

Since in some cases the machine can not protect against an operator-generated human error, many dialysis machines require the operator to enter information twice before the microcontrollers will accept the information. The theory behind the double-entry requirement is that the operator is more likely to recognize an error if the operator is required to check, view or consider the entered information twice. Generally the first entry results in the information being recorded in memory and then displayed to the operator. After the operator has again entered the same information, the microcontroller compares the first and second entries. If the two entries are the same, the first entry previously recorded in memory will be transferred to the control system and safety system microcontrollers for use during the treatment. Other typical information entry techniques used in dialysis machines display the second entry in a separate location from the display of the first entry. The operator must then mentally compare the two entered values, and if they are equal, accept the entered value. In this double-display technique, the dialysis machine does not make the comparison, but instead leaves the comparison to the operator.

While the double-entry and double-display techniques have generally proved successful, they are somewhat tedious, repetitious and time-consuming for the operator. The typical machine setup procedure requires the entry of a significant number of different values, and the time associated with the double-entry detracts from the other activities required to ready the machine for treatment. Furthermore, the repetitiveness of the entries can lead to a type of monotony which may cause the operator to be less vigilant in visually comparing the two displayed values, or which results in a certain level of tension and tedium resulting from making the second entry, or which results in frustration when the operator encounters difficulty in correctly entering the information in sequential entries.

These and other considerations have contributed to the evolution of the present invention which is summarized below.

SUMMARY OF THE INVENTION

One of the significant aspects of the present invention pertains to an information entry system and method which requires the operator to enter the value only a single time, but which achieves a standard of validation that satisfies existing safety standards relating to the entry of information in dialysis machines. Another aspect of the invention relates to alerting the operator if the information which has been entered has been corrupted by the machine. Another aspect of the invention relates to entering and validating information in a manner which will assure that both the control system and safety system microcontrollers validly receive the same information which the operator has entered and approved. A further aspect of the invention relates to an information entry validation technique in which the proper functionality of certain input/output (I/O) devices is confirmed as an adjunct of the information entry. Still another aspect of the invention relates to a convenient and user-friendly technique for entering and confirming information used by a dialysis machine.

In accordance with these and other aspects, the present invention pertains to a system and method for a dialysis machine in which entered control and safety information is validated. The machine includes an information entry device, for example a touch screen, and a display device, for example a cathode ray tube (CRT). A safety system of the machine receives information entered from the entry device. The entered information is first converted into a first form using a first conversion relationship. The information in the first form is next converted into a second form using a second conversion relationship. The second conversion relationship is different from the first conversion relationship. Thereafter the information in the second form is converted back to the first form using the first conversion relationship. The information in the first form which resulted from the third conversion is displayed on a display device for acceptance for rejection by the operator.

The multiple sequential conversions provide the operator with an opportunity to evaluate the internal functionality of the machine and to determine if the machine has corrupted the entered information. A malfunction will usually result in the information being displayed improperly or in an unusual form. Conversion of the information from one form into another form is likely to reveal that a corruption problem has occurred. Presentation of the displayed information only after and based on the sequential multiple conversions assures an opportunity for the operator to evaluate the entries for accuracy. With sequential entries, each new entry is subjected to the same series of conversions, but the collective value of the previous sequential entries is displayed. The re-display of the previously entered information repeatedly presents the information to the operator, but in a naturally-appearing manner which does not create the impression of duplicity, redundancy or multiple confirmation. As a result, the entered information is validated in a more time-conserving and reliable manner, while reducing the operator's workload without compromising the degree of validation.

Preferred aspects of the invention involve using an ASCII conversion relationship for the first conversion and a floating point numeric conversion relationship for the second conversion. A font table is employed to derive the information displayed to the operator. The use of the font table further confirms a state of proper functionality in the machine by notifying the operator if the characters presented are improper or unusual. Improper or unusual characters would result from an error in the font table. Furthermore using the same font table to derive the characters for all of the displayed information has the additional benefit of confirming significant parts of the overall machine functionality, apart from the information entry.

Other preferred aspects of the invention involve storing the entered information in the second form into a third permanent memory location after the value has been previously stored in the second memory location. After the operator has accepted all of the values previously entered, the information in the second and third memory locations is compared. If the comparison reveals equal values in both locations, the information in the third memory location is displayed to the operator in a location which is different from that location where the same information was displayed while the operator entered the information. The information displayed from the third memory location is thereafter transferred to the control system of the dialysis machine for use during operation of the machine. An error detecting code is also calculated from the information in the second memory location and is stored in association with the information in the third memory location. The error detecting code is employed to validate the transfer of the information to the control system and/or the safety system.

Many other preferred aspects of the present invention, and a more complete appreciation of the present invention and its scope, may be understood from the accompanying drawings, which are briefly summarized below, from the following detailed description of a presently preferred embodiment of the invention, and from the appended claims.

DETAILED DESCRIPTION

Figure 1:
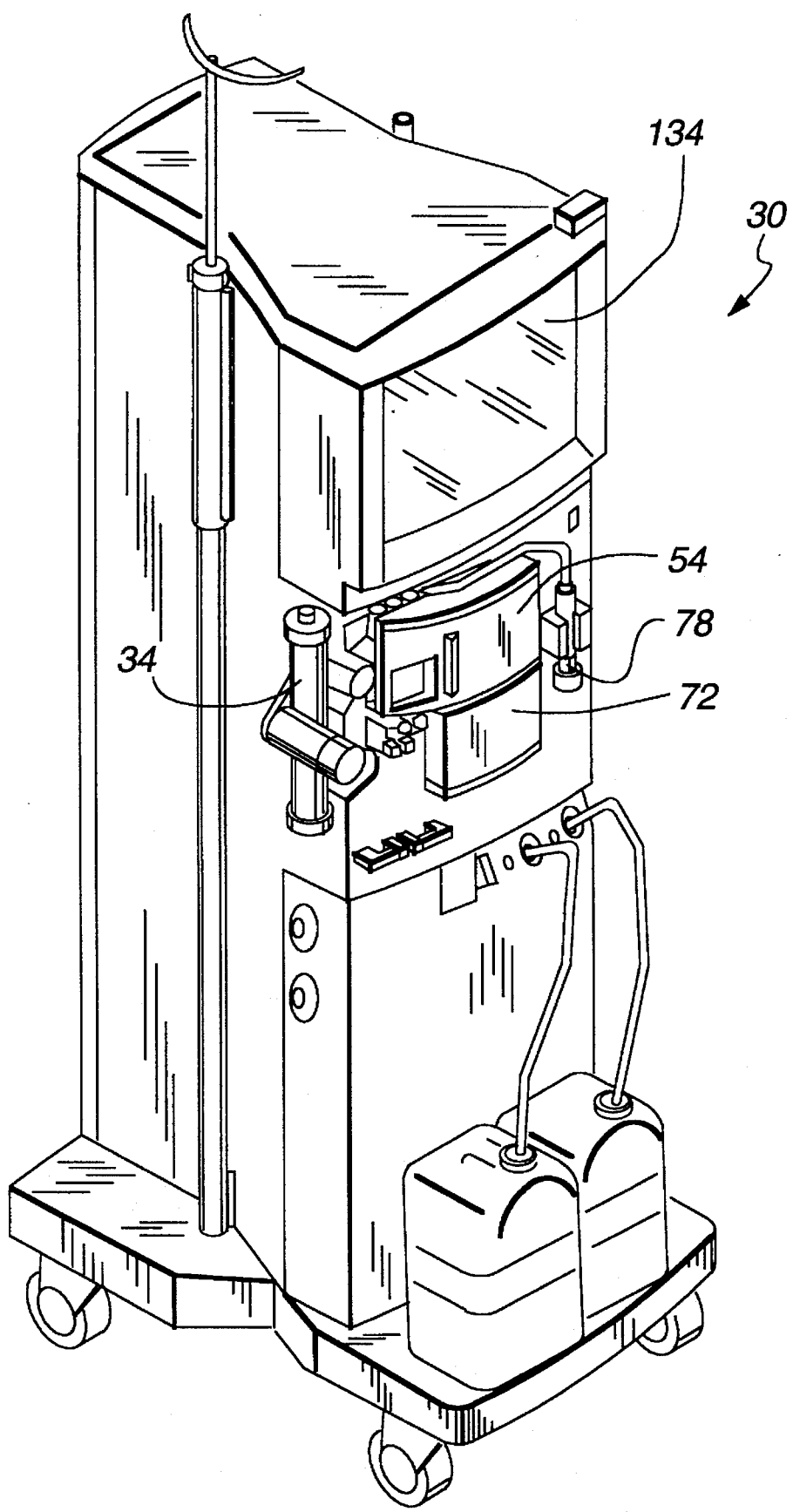
FIG. 1 is a perspective view of a dialysis machine which incorporates the present invention.

An example of a dialysis machine with which the present invention may be advantageously employed is shown at 30 in FIG. 1. The dialysis machine 30 includes the devices generally shown in FIG. 2, and those devices establish an extracorporeal flow path and a hydraulics flow path. The extracorporeal flow path conducts blood from a patient 32 to a dialyzer 34, and then returns the blood from the dialyzer 34 to the patient 32. The hydraulics flow path conducts dialysate from a supply 36 to the dialyzer 34, and then returns the used dialysate to a waste drain 38.

The blood in the dialyzer 34 is confined to a blood chamber 40, and the dialysate in the dialyzer 34 is confined to a dialysate chamber 42. The blood chamber 40 and the dialysate chamber 42 are separated by a microporous or other type of dialysis medium 44. The waste products contained in the blood within the blood chamber 40 are transferred through the medium 44 by osmosis, ionic transfer or flow transfer to the dialysate in the dialysate chamber 42. Desirable components of the dialysate in the dialysate chamber 42 may also be transferred to the blood in the blood chamber 40 by the same mechanisms. In this manner, the waste products are removed from the patient's blood, and the cleansed blood is returned to the patient 32. The used dialysate flowing from the dialysate chamber 42 discharges the waste products into the drain 38 which may be a public sewer.

The elements of the extracorporeal flow path include at least one blood pump 46 which controls the flow of blood from the patient 32. An arterial line or tubing 48 extends through an arterial clamp 50 to a blood handling cartridge 52. The blood handling cartridge 52 is normally retained behind a door 54 of the machine 30 when used. The blood handling cartridge 52 is not shown in FIG. 1. The blood pump 46 also is located behind the door 54 and adjacent to the cartridge 52. The blood pump 46 is typically a peristaltic pump in dialysis machines.

Blood flows through the arterial line 48 and into an arterial chamber 56 of the cartridge 52. The blood pump 46 draws blood from the arterial chamber 56 through a pump tubing 58 which is squeezed or pinched by a rotating rotor 60 against a stationary raceway 62, in the typical manner of peristaltic pumps. The blood within the pump tubing 58 which is trapped rotationally in front of the point where the rotor 60 pinches the pump tubing is propelled through the pump tubing 58 and into a manifold 64 of the cartridge 52. A tubing 66 conducts the blood from the manifold 64 of the cartridge 52 into a blood inlet of the dialyzer 34.

The cleansed blood flowing from an outlet of the dialyzer 34 is transferred through a tubing 67 back to a venous chamber 68 of the cartridge 52. Blood from the venous chamber 68 is removed from the cartridge 52 through a venous tubing or line 70. Although not shown in FIG. 2, a venous blood pump similar to the arterial blood pump 46 may be located in the venous line to assist in forcing the blood back into the patient 32 or to regulate the flow of blood through the extracorporeal flow path. If employed, the venous blood pump is positioned behind a second door 72 of the dialyzer machine 30 shown in FIG. 1.

After leaving the venous chamber 68 the blood flows through the venous line 70 to an air detector 74. The air detector 74 derives signals related to any air in the venous line 70. If an excessive or dangerous amount of air is present, a venous line clamp 76 will immediately close to terminate the flow of blood through the venous line 70 before the air reaches the patient 32.

Because the blood in the extracorporeal flow path is prone to clot, a blood anticoagulant such as heparin is injected into the extracorporeal flow path. The anticoagulant is slowly delivered from a syringe 78 as a result of a linear driver mechanism (not shown) moving a plunger 80 into the syringe 78. Anticoagulant from the syringe 78 is introduced into the arterial chamber 56 of the cartridge 52 through a tubing 82. The syringe 78 and the linear driver mechanism are typically referred to as an anticoagulant pump.

The elements of the hydraulics flow path include a number of different valves (some of which are not shown) and a dialysate pump 84 which draws dialysate from the supply 36. The supply 36 is typically a mixture of chemicals and water which the dialysis machine prepares as the dialysate is used, or a previously prepared quantity of dialysate which is delivered to the dialysis machine 30. The dialysate pump 84 draws the dialysate from the supply 36 and delivers it through a dialysate supply tubing or line 86 to an inlet of the dialysate chamber 42 of the dialyzer 34. The dialysate flows past the medium 44 where it absorbs the waste products from to the blood in the blood chamber 40. Any beneficial components within the dialysate which are desired to be transferred to the blood pass through the medium 44 and into the blood in the blood chamber 40.

Prior to entering the dialyzer 34, the dialysate is heated in a heater 88 to the normal human body temperature. The temperature of the dialysate entering the dialyzer 34 should be at body temperature to avoid removing or transferring heat to or from the patient. Excessively warm dialysate will harm blood cells. Excessively cool dialysate will chill the patient. Temperature sensors (not shown) are located in the dialysate supply line 86 to monitor the temperature of the dialysate.

Conductivity sensors (not shown) are present in the dialysate supply line 86 to measure the conductivity of the dialysate. The desired level of ionic transfer between the blood and the dialysate is achieved by predetermined conductivity characteristics of the dialysate.

The used dialysate containing the waste products is removed from the dialysate chamber 42 through a dialysate waste tubing or line 90 by operation of a drain pump 94. The dialysate containing the waste products is delivered by the drain pump 94 to the waste drain 38. The waste drain 38 may be a separate container which accumulates the used dialysate and accumulated waste products, or it may simply be a public sewer.

As a safety precaution, bypass valves 96 and 98 are positioned at the inlet and the outlet of the dialysate chamber 42, respectively. The bypass valves 96 and 98 are connected by a bypass line 100. Normally the bypass valve 96 directs the inflow of dialysate into the dialysate chamber 42, and normally the bypass valve 98 directs the outflow of dialysate into the dialysate waste line 90. If a safety condition is detected, the bypass valves 96 and 98 are operated to their alternative states, thereby directing the flow of dialysate through the bypass line 100, and bypassing the flow of dialysate around the dialyzer 34.

Figure 3:
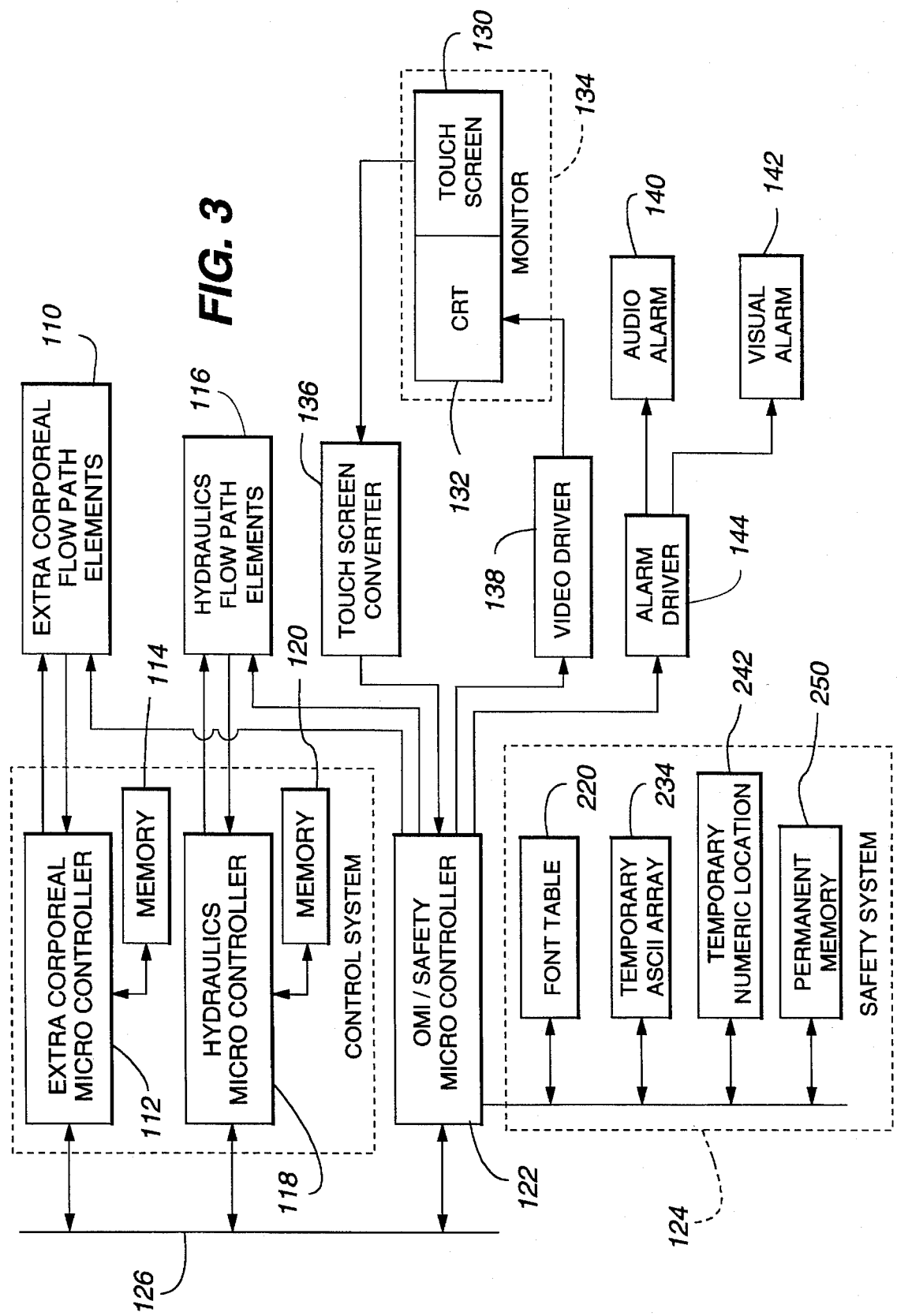
FIG. 3 is a block diagram of the control system and safety system of the dialysis machine shown in FIGS. 1 and 2, illustrating the components which accomplish information entry validation according to the present invention.

The elements of the extracorporeal flow path, which have generally been described above, are shown and referenced generally at 110 in FIG. 3. The extracorporeal flow path elements 110 are controlled by an extracorporeal microcontroller 112 or other similar processing device, as shown in FIG. 3. The extracorporeal microcontroller 112 executes a program recorded in a memory 114 to control the extracorporeal flow path elements 110.

The elements of the hydraulics flow path, which have generally been described above, are also shown and referenced generally at 116 in FIG. 3. The hydraulics flow path elements 116 are controlled by a hydraulics microcontroller 118 or other similar processing device. The hydraulics microcontroller 118 executes a program recorded in memory 120 to control the hydraulics flow path elements 116.

An operator/machine interface (OMI) and safety microcontroller 122 is also connected to the extracorporeal flow path elements 110 and the hydraulic flow path elements 116. The OMI and safety microcontroller 122 monitors the operating conditions in the extracorporeal and hydraulics flow paths, and upon detecting a potentially risky condition for the patient, assumes control over the extracorporeal and hydraulics flow path elements 110 and 116 to place them into a safe patient state. The safety microcontroller 122 executes a program recorded in its memory 124 to monitor the operating conditions of the dialyzer machine 30 and the patient 32 during dialysis treatment, to determine potentially hazardous conditions, and to place the dialyzer machine in a safe patient state upon the detection of a hazardous condition.

The three microcontrollers 112, 118 and 122 communicate with one another to exchange information and confirm proper functionality, among other things, by use of a bus or network 126. In general, the extracorporeal microcontroller 112 and the hydraulic microcontroller 118 are generally responsible for the control functions of the dialysis machine. The safety microcontroller 122 is responsible for the safety functions of the dialysis machine.

Use of the three microcontrollers meets the safety standards for dialysis machines. In general, the safety standards emphasize redundancy to avoid the possibility that a single equipment failure will place the patient in a hazardous condition. If the failure of a control system microcontroller occurs, the safety system microcontroller is capable of placing the dialysis machine in the safe patient state. For example, should the hydraulics microcontroller 118 fail, the safety microcontroller 122 can assume control over the hydraulics flow path elements 114 to achieve the safe patient state. Similarly, should the extracorporeal microcontroller 112 fail, the safety microcontroller 118 will assume control over the extracorporeal flow path elements 110 to achieve a safe patient state. If the safety microcontroller 122 fails, the extracorporeal and hydraulics microcontrollers are capable of placing the dialysis machine in a safe patient state.

Although it is typical to use multiple microcontrollers in dialysis machines to meet the safety standards, a dialysis machine which meets safety standards while using only a single microcontroller for executing the control system and safety system functions is described in the above mentioned U.S. patent application for a Single Microcontroller Execution of Control and Safety System Functions in a Dialysis Machine. The present invention may be utilized with either single or multiple microcontroller dialysis machines.

Because it is necessary to enter various types of safety and operational information to achieve a particular dialysis treatment or prescription for a patient, the safety standards also govern the entry of information into the dialysis machine. In general, those standards are concerned with confirming to the operator that the information entered into the machine is what the operator intends. It is also important that the operator know that the information entered is the information accurately stored in the memories 114, 120 and 124. The other general safety regarding information entry is that the safety microcontroller 122 and the control system microcontrollers 112 and 118 commence operations using the same entered information. If the safety and the control systems do not start with the same information, it will be extremely difficult or impossible to detect a difference in operation of the two systems, and such a difference could give rise to a safety situation.

The present invention achieves a more convenient and natural approach to entering and validating information into a dialysis machine, without compromising the safety standards and while simultaneously supplying better information to the operator concerning the safety and operating conditions of the dialysis machine.

The operator-machine interface (OMI) is the means by which information is entered into the dialysis machine and by which the entered information is validated back to the operator. The OMI functionality is incorporated with that of the safety microcontroller 122 shown in FIG. 3, or could be performed by its own microcontroller. By entering all information through the safety microcontroller 122, it is assured that the control system microcontrollers 112 and 118 will start with the same values or information which is initially recorded in the safety microcontroller 122.

The preferred means for entering and for displaying to the entered information back to the operator is a conventional touch screen 130 attached to a front viewing surface of a conventional cathode ray tube (CRT) 132. The touch screen 130 and the CRT 132 are incorporated in a monitor 134 of the machine 30 shown in FIG. 1.

The touch screen 130 is a thin transparent sheet assembly which physically overlays a front viewing surface of the CRT 132. The overlaying relationship is generally illustrated in FIG. 3. With the touch screen 130 in position, the images displayed on the viewing surface of the CRT 132 define locations which the operator may select by applying finger pressure to the touch screen 130 at the location of the images. The touch screen 130 generates signals which describe the X-Y coordinates of the position where the finger pressure is applied. Those signals are supplied to a conventional touch screen converter 136 which converts the X-Y signals from the touch screen 130 into corresponding signals which are supplied to the safety microcontroller 122. The programmed functionality of the safety microcontroller 122 correlates the signals from the touch screen converter 136 with the location of the images displayed on the viewing surface of the CRT 132. The correlation is possible because signals are supplied by the safety microcontroller 122 to a video driver 138 to control the position and details of the images displayed on the viewing screen of the CRT 132. By correlating the X-Y position signals from the touch screen converter 136 with the viewing images defined by the signals delivered to the video driver 138, the microcontroller 122 is able to recognize those selections made by the operator touching the touch screen 130. This functionality is typical and well known for touch screen input and output (I/O) devices.

To alert the operator in the case of a safety or other condition, an audio alarm 140 and a visual alarm 142 are used in the dialysis machine 30. The audio and visual alarms 140 and 142 are controlled by a driver 144. The driver 144 responds to control signals supplied by the safety microcontroller 122 to create a visual alarm or signal or an audio alarm or signal when necessary.

Figure 4:
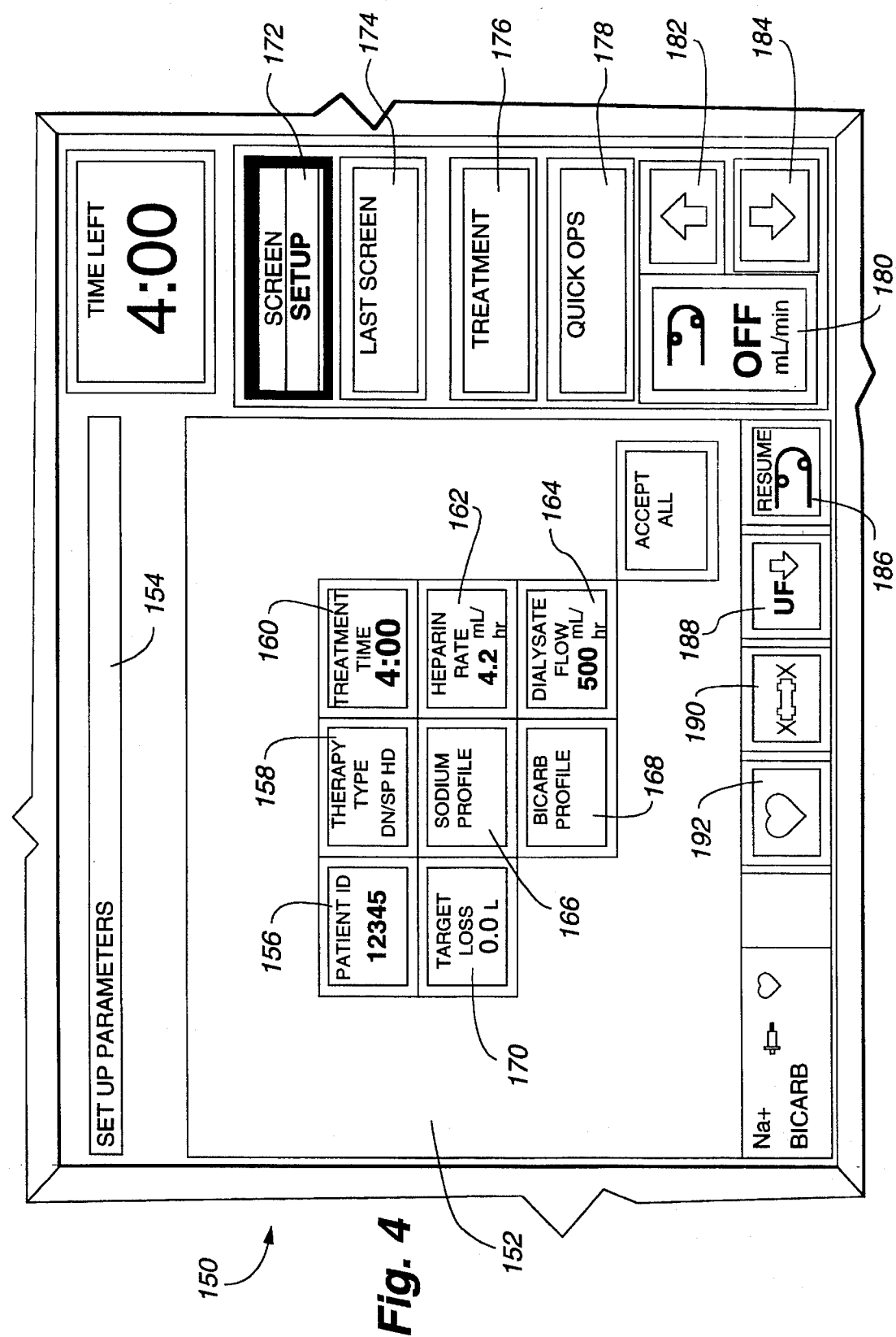
FIG. 4 is an illustration of a screen display initially presented on a monitor of the dialysis machine shown in FIGS. 1 and 3, prior to entry of information.

An example of a visual display created by the safety microcontroller 122 and the video driver 138 is shown in FIG. 4. The visual display is shown as it appears on the viewing screen of the CRT 132, and it will therefore be referred to as a display screen 150. The display screen 150 is divided into different areas which present information concerning the functions and status of the dialysis machine. A relatively large main window area 152 shows a number of setup parameters for controlling the dialysis machine during treatment, in this example. A title bar 154 indicates that setup parameters shown in the main window 152.

The eight setup parameters shown in the main window 152 are the patient identification number at 156, the type of dialysis treatment at 158, the time for the dialysis treatment at 160, the heparin infusion rate during the treatment at 162, the dialysate flow rate during treatment at 164, the profile for delivering sodium in the dialysate during the treatment at 166, the profile for delivering bicarbonate in the dialysate during the treatment at 168, and the target loss or volume of waste products to the removed from the patient's blood during the treatment at 170. Other types of setup parameters could be displayed. The patent application described above for a Graphical Operator Machine Interface and Method for Information Entry and Selection in a Dialysis Machine describes an advantageous technique of selecting parameters and programming the dialysis machine.

In addition to the main window 152, the right hand border (as shown) or some other selected area of the display screen 150 is occupied by images which allow the operator to select functional features of the display for purposes of entering information or monitoring the performance of the machine for the treatment. Touching a screen image 172 allows the operator to index among various displays and, for example, select the setup parameters, as is shown of at 172 and 154. Touching the touch screen above a last screen image 174 allows the operator to toggle between the present display screen 150 and the previously presented display screen. Touching a treatment setup image 176 allows the operator to select from a list a dialysis functions that are expected to occur in conjunction with each treatment. A quick OPS image 178 allows the operator to select from a list of easy access functions that are not necessarily expected in each treatment.

The on and off operation of the blood pump 46 (FIG. 2) is controlled by touching the blood pump icon or image 180. The blood pump is turned on and off with each touch. The rate of blood pump operation may be adjusted incrementally upward or incrementally downward by touching an up arrow image 182 or a down arrow image 184, respectively. Continual finger pressure on either of the arrow images 182 or 184 causes repeated incrementation. When operating, the blood pumping rate is displayed in the location where the word "off" appears in the blood pump image 180.

The bottom border or other designated area of the display screen 150 also includes a number of images or icons which represent control and monitoring conditions associated with the patient and the dialysis machine. The image at 186 which states "resume" is selected to resume treatment if the blood pump operation has been stopped.

The image at 188 which states "UF" accompanied by a downward pointing arrow is selected when it is desired to reduce the amount of ultrafiltration which may be occurring during a treatment. Ultrafiltration is a well-known aspect of some types of dialysis treatments which involves the direct introduction of an ultrafiltration solution into the blood. The ultrafiltrate may be introduced into the extracorporeal flow path prior to the blood reaching the dialyzer 34 (FIG. 2) or after the blood has passed through the dialyzer. Of course, if ultrafiltration is not used during the treatment, no functionality will be achieved by touching the ultrafiltration image 188.

Figure 2:
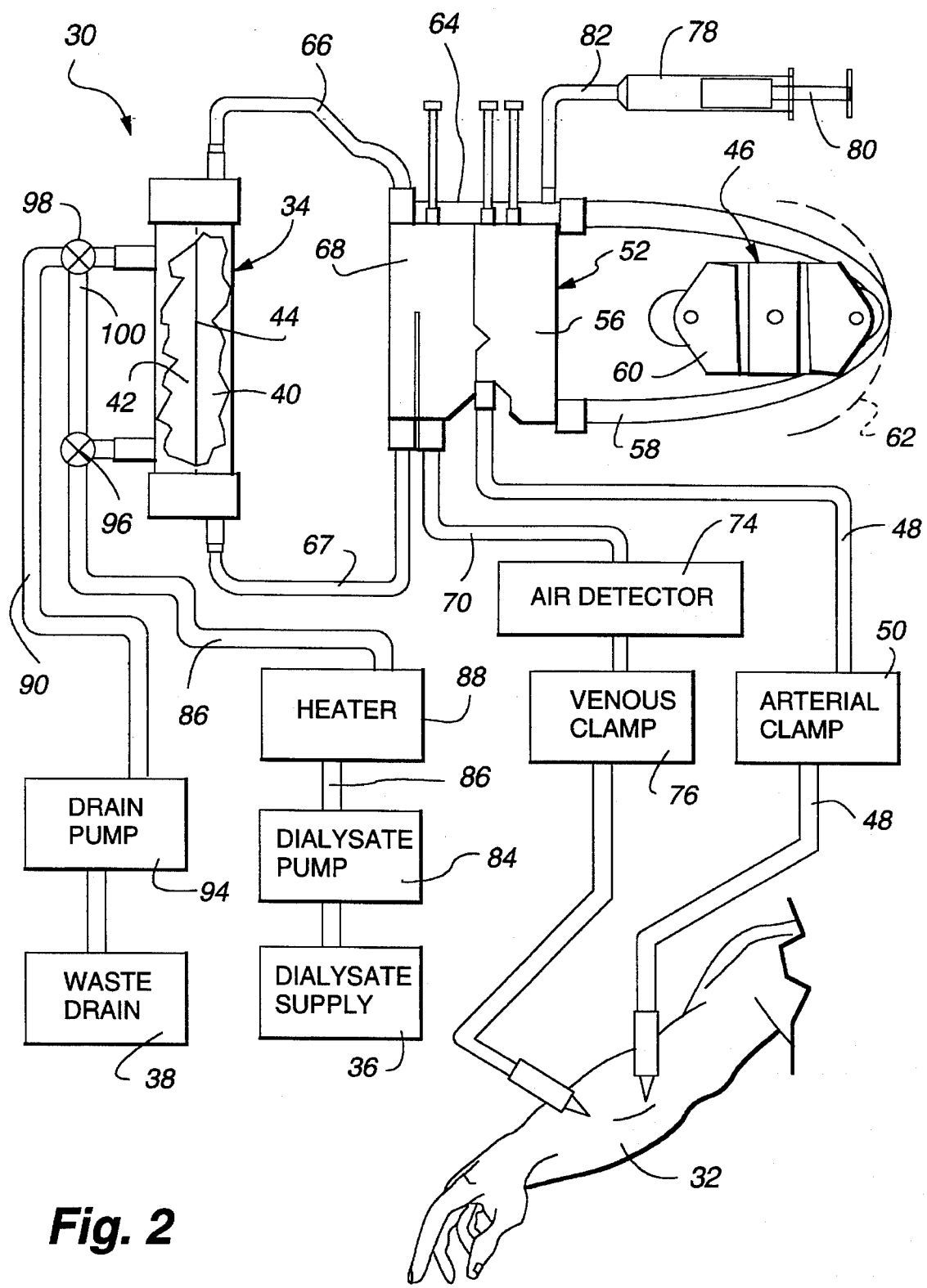
FIG. 2 is a generalized view illustrating a dialyzer, an extracorporeal flow path for blood from a patient through the dialyzer, and a hydraulics flow path for dialysate through the dialyzer, as are present during treatment of a patient with the dialysis machine shown in FIG. 1.

The image displayed at 190 is an icon representative of the dialyzer 34 (FIG. 2). Touching the dialyzer image 190 results in bypassing the dialysate flow around the dialyzer. The image or icon of a heart at 192 allows the operator to obtain information concerning the patient's blood pressure, if a blood pressure monitoring functionality is a part of the dialysis machine and a blood pressure cuff is connected to the patient.

Organization of the display screen 150 in this manner allows a more convenient, time-conserving, reliable and safety-promoting approach to setting up the dialysis machine and operating the machine during the treatment, as is described more completely in the above referenced application for a Graphical Operator Machine Interface and Method for Information Entry and Selection in a Dialysis Machine.

One of important safety-promoting aspects of the display screen 150 is its interaction with the operator and with the functionality of the OMI/safety microcontroller 122 (FIG. 3) in validating information, particularly numeric values, entered by the operator during the setup of the machine for dialysis treatments and during modification of the operating parameters of the machine while the dialysis treatment is progressing. The aspects of the information validation technique according to the present invention are represented in the flow chart shown in FIGS. 9A and 9B, and are illustrated in the screen displays shown in FIGS. 4–8.

Figure 9A:
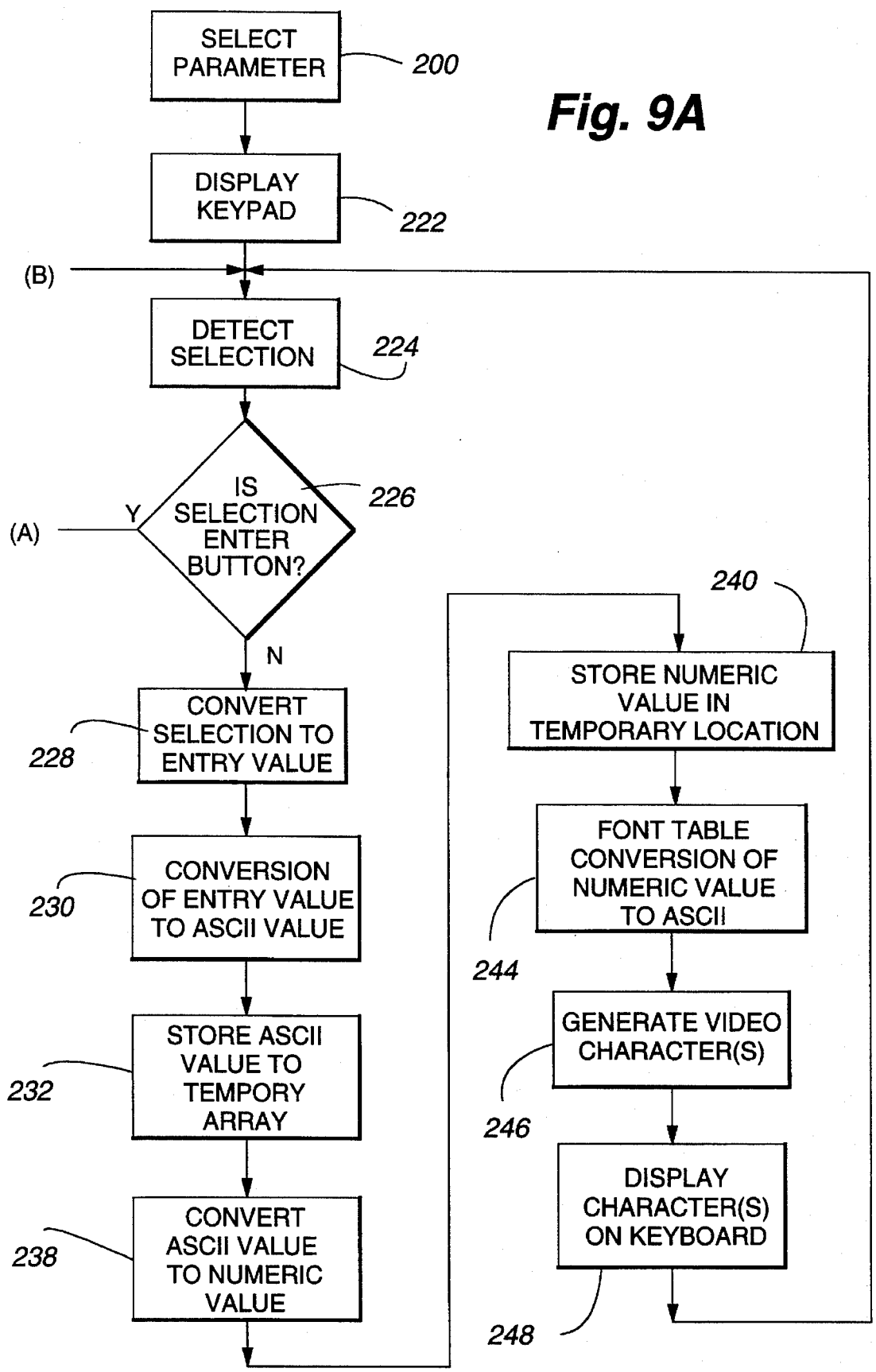
FIGS. 9A and 9B collectively form a single flow chart which illustrates steps involved in the entry and validation of information by a operator machine interface and safety microcontroller shown in FIG. 3.
Figure 9B:
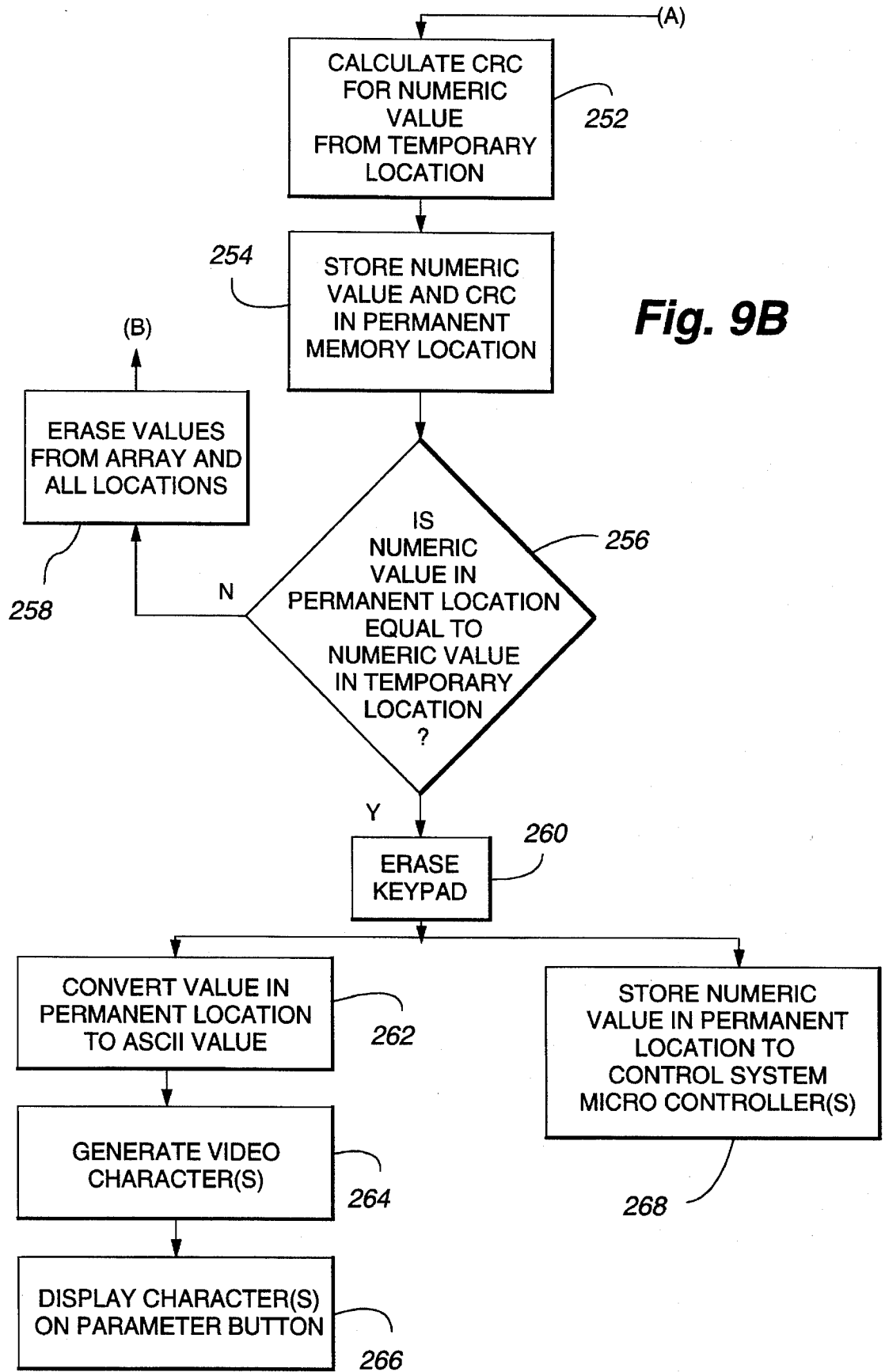

The steps of the technique shown in the flow chart of FIGS. 9A and 9B are executed by the OMI/safety microcontroller 122 in conjunction with the memory 124 connected to the microcontroller 122. Each of the steps shown in the flow chart of FIGS. 9A and 9B are separately identified by reference numbers for convenience of description.

In order to employ the information validation technique of the present invention, the operator must first select a parameter to be modified or established. The selection of the parameter is shown in FIG. 9A at step 200. The selection is also shown in FIG. 4 where the touch screen is touched in the area above the screen image 172. The screen image 172 is highlighted and the word "setup" appears. The fact that the setup parameters have been selected appears in the title bar 154. The setup parameters which are available to the established or modified are shown in the main window 152.

Figure 5:
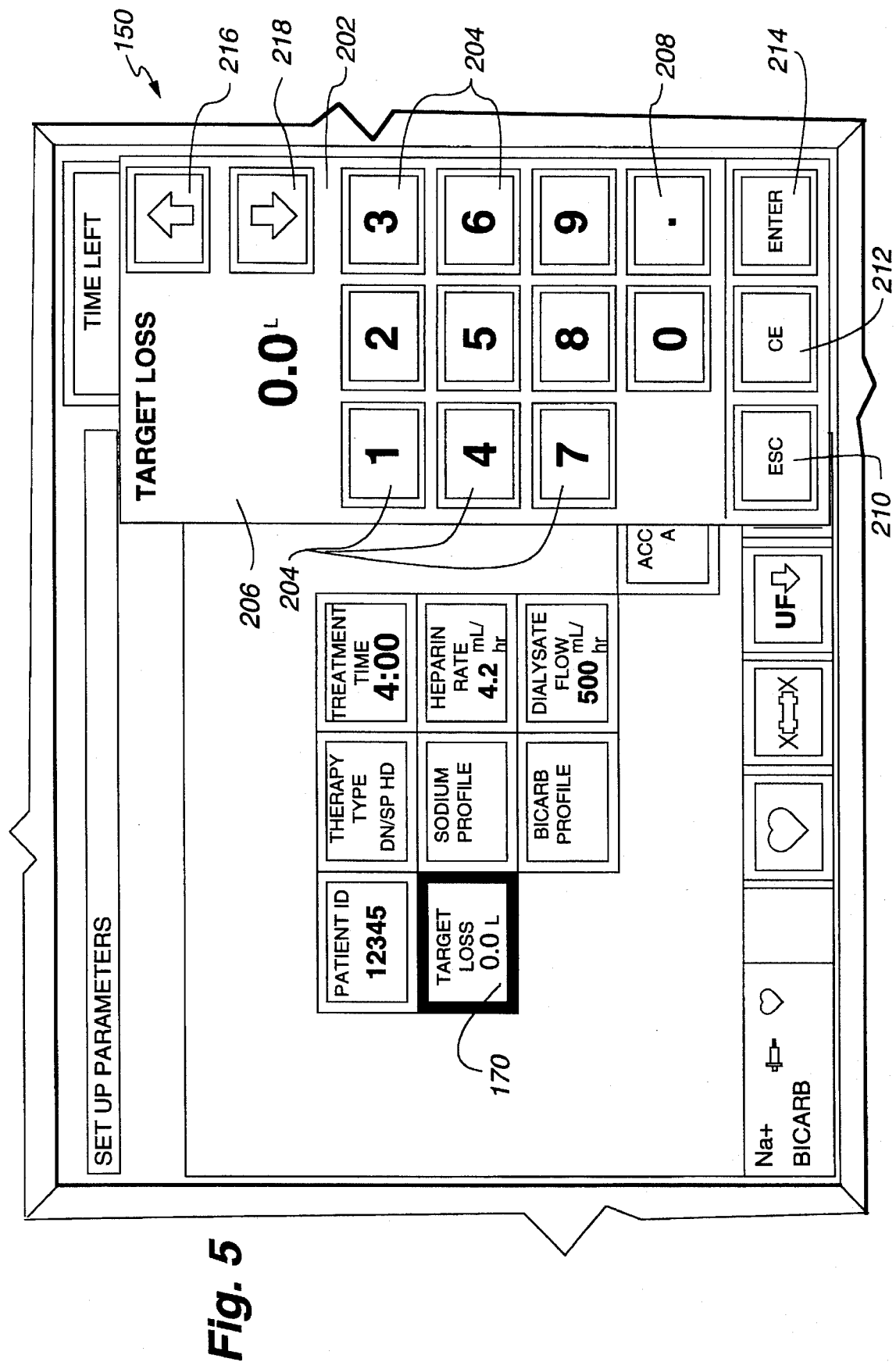
FIG. 5 is an illustration similar to that shown in FIG. 4, upon which a keypad is displayed for the entry of information.

For example, assume the operator desires to establish or change the value of the target loss of waste volume to the removed from the patient, as is displayed at 170. The operator presses the touch screen in the area above the target loss image 170 to select the target loss setup parameter. The target loss image 170 is highlighted, as shown in FIG. 5, thereby indicating to the operator that the target loss parameter can now be established or modified.

If the parameter selected for modification or establishment is one which allows selection of discrete numeric values, a keypad 202 (FIG. 5) is displayed on the display screen 150. The signals which define the keypad display 202 are created by the microcontroller 122 and the video driver 138 (FIG. 3), and the CRT 132 (FIG. 3) creates the keypad 202. The keypad 202 is presented in place of some of the images which otherwise occupy the right hand and bottom border areas of the display screen 150, as can be seen by comparing FIGS. 4 and 5.

The keypad 202 includes areas which define numeric buttons 204, a selected parameter display area 206 which presents a title corresponding to the parameter selected at 170, a decimal point button 208, an escape button 210, a clear button 212, and an enter button 214. In addition, an up arrow 216 and a down arrow 218 are located adjacent to the display area 206 to be used for incrementing the value of the parameter shown in the display area 206, either upwardly or downwardly.

The logical and sensible display of the keypad 202 provides the very important information that the safety microcontroller 122 and a font table 220 (FIG. 3) of the memory 124 are correct and operating properly. The font table 220 contains information from which the signals for creating the numbers in the keypad 202 are derived. If the numbers on the keypad 202 are not properly formed, or if the numbers are not located in the positions where the operator expects them to be located, a malfunction can be immediately detected. The operator will recognize the malfunction as making the dialysis machine unreliable. Thus, the use of the font table 220 to create the keypad 202 is an important aspect of information supplied to the operator concerning the validation and proper functionality of the dialysis machine. Assuming that the information presented in the keypad 202 is correct, the operator will continue with the information validation technique of the present invention and use of the dialysis machine.

The described functionality which presents the keypad 202 is shown at step 222 in FIG. 9A. After displaying the keypad at step 222, the program flow ceases until an entry or selection made by touching the screen is detected at 224. A determination is made at 226 whether the selection detected at step 224 was from the enter button 214 (FIG. 5) or from some other button from the keypad display 202. The purpose of the enter button 214 is to represent the final acceptance of all of the information or numeric values which have just been entered. Until the operator finally accepts the selected information by touching the enter button 214 (FIG. 5), the program flow will continue at the step 228.

The step 228 involves converting the X-Y signals from the touch screen 130 into an entry value obtained by touching the numeric buttons 204 (FIG. 5), by use of the touch screen converter 136 (FIG. 3) and the correlation of the signals from the converter 136 with the signals generated by the microcontroller 122 to display the numeric values in the keypad 202 (FIG. 3).

The entry value derived at step 228 is thereafter converted at step 230 into an ASCII value. Typically the entry value determined at step 228 is directly memory mapped to an ASCII value. ASCII values are employed for the purpose of displaying all of the numbers and characters.

Rather than immediately display the ASCII value derived from the step 230, the information entry validation technique of the present invention employs additional important steps to confirm the accuracy and acceptability of the entered value to the operator while simultaneously confirming the proper operation and acceptance of the value by the safety microcontroller. After the entered value is converted to the ASCII value at step 230, the ASCII value is stored at step 232 in a temporary array 234 (FIG. 3) of the memory 124. The temporary memory array 234 is a collection of memory locations or cells in which the ASCII value for each entry is separately stored. The individual locations or cells of the array 234 to which the ASCII values derived from each entry are separately stored are shown individually at 236a, 236b, 236c, . . . 236n in FIG. 10.

After the ASCII value has been stored in the temporary array at step 232, the microcontroller 122 (FIG. 3) immediately converts the stored ASCII value into a different representation of the same information or value represented by the ASCII value, such as a numeric value, preferably a floating point numeric value. The conversion to the different form is shown at step 238 in FIGS. 9A and 10. The numeric value derived at 238 is stored at 240 in a temporary numeric memory location 242 (FIG. 3) of the memory 124. The temporary numeric memory location 242 is a segment or location within the memory 124 which the microcontroller 122 designated for receiving the numeric value.

Figure 6:
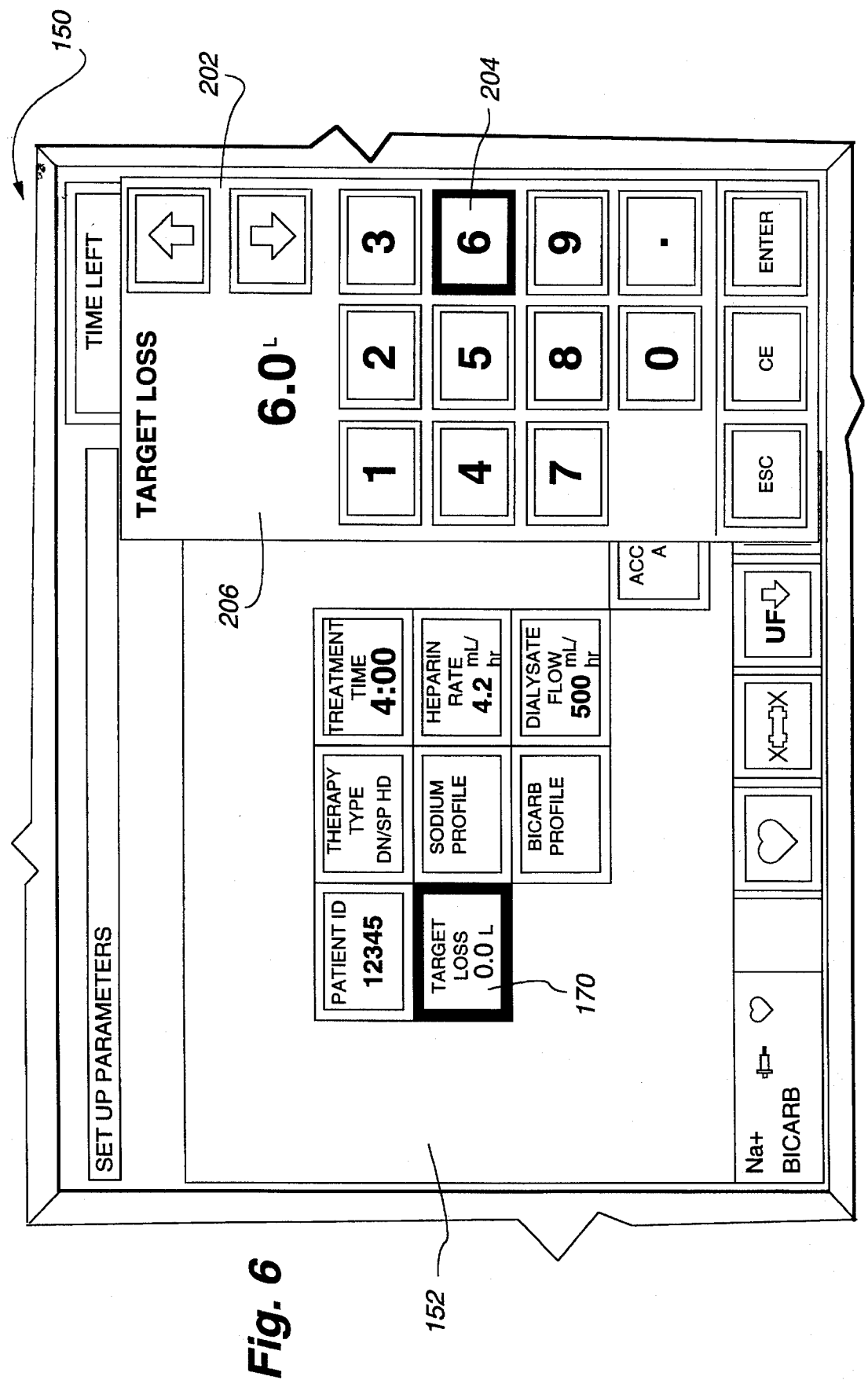
FIGS. 6, 7 and 8 are screen displays similar to those shown in FIGS. 4 and 5, which illustrate other displays during the entry and validation of information according to the present invention.

Using the numeric value stored in the temporary memory location at step 240, the numeric value is immediately converted back into an ASCII value at step 244. The font table 220 (FIG. 3) may be used in this conversion if the inherent functionality associated with the conversion does not immediately convert the floating point numeric value into an ASCII value. The ASCII value thus derived is thereafter applied to the video driver 138 (FIG. 3), and in response, the video characters corresponding to the ASCII value are generated, as shown at 246 in FIG. 9A. The CRT 132 (FIG. 3) displays the character to the operator as shown at 248 in FIG. 9A. The display of the value appears in the display area 206 of the keypad 202 as shown in FIG. 6. FIG. 6 illustrates the circumstance where the numeric "6" button 204 has been selected by finger pressure, resulting in the number "6" being presented in the display area 206 (FIG. 6). In the example shown in FIG. 6, the entered value of "6" is the first value of 3 values to be entered.

After the selected characters are displayed in the display area 206 (FIG. 6) of the keypad as shown at step 248 in FIG. 9A, the program flow reverts back to the step at 224 to detect another entry or selection of information. With each subsequent entry of information the steps beginning at 228 and ending at 248 are executed. However, each separate information selection is stored in a separate memory cell 236a, 236b, 236c . . . 236n, shown in FIG. 10. In the example shown by comparing FIGS. 6 and 7, the first ASCII entry (the numeric value "6") is stored in the cell 236a; the second ASCII entry (the decimal point) is stored in cell 236b; and the third ASCII entry (the numeric value "3") is stored in cell 236c. If the entered information included additional selected values, all of the additional entries would be stored to subsequent memory cells and the last or nth ASCII entry would be stored in the last cell 236n.

Figure 10:
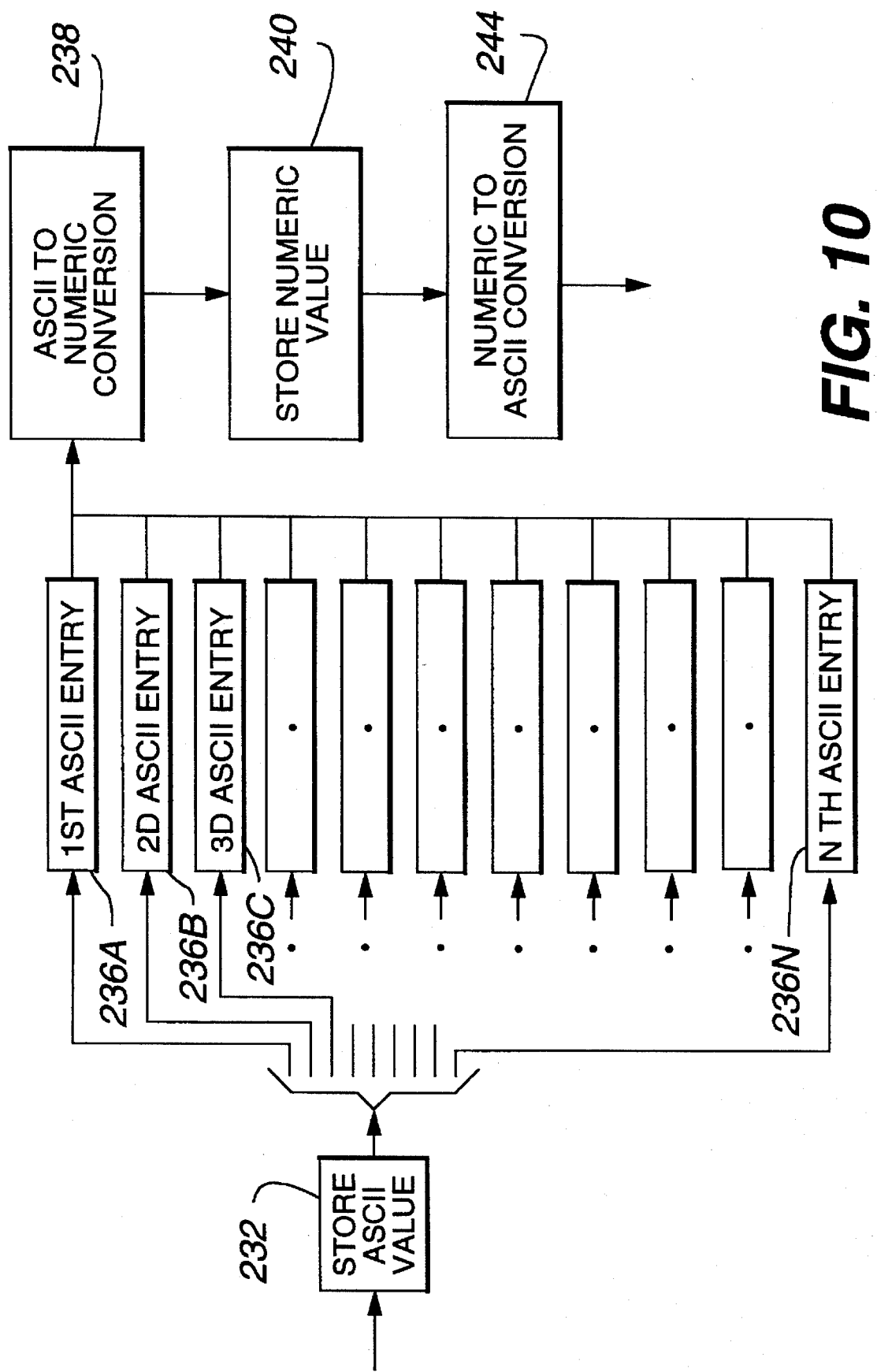
FIG. 10 is another illustration of some of the steps in the flow chart shown in FIG. 9A and the relationship of those steps with a temporary memory array and a temporary numeric memory shown in FIG. 3.
Figure 11:
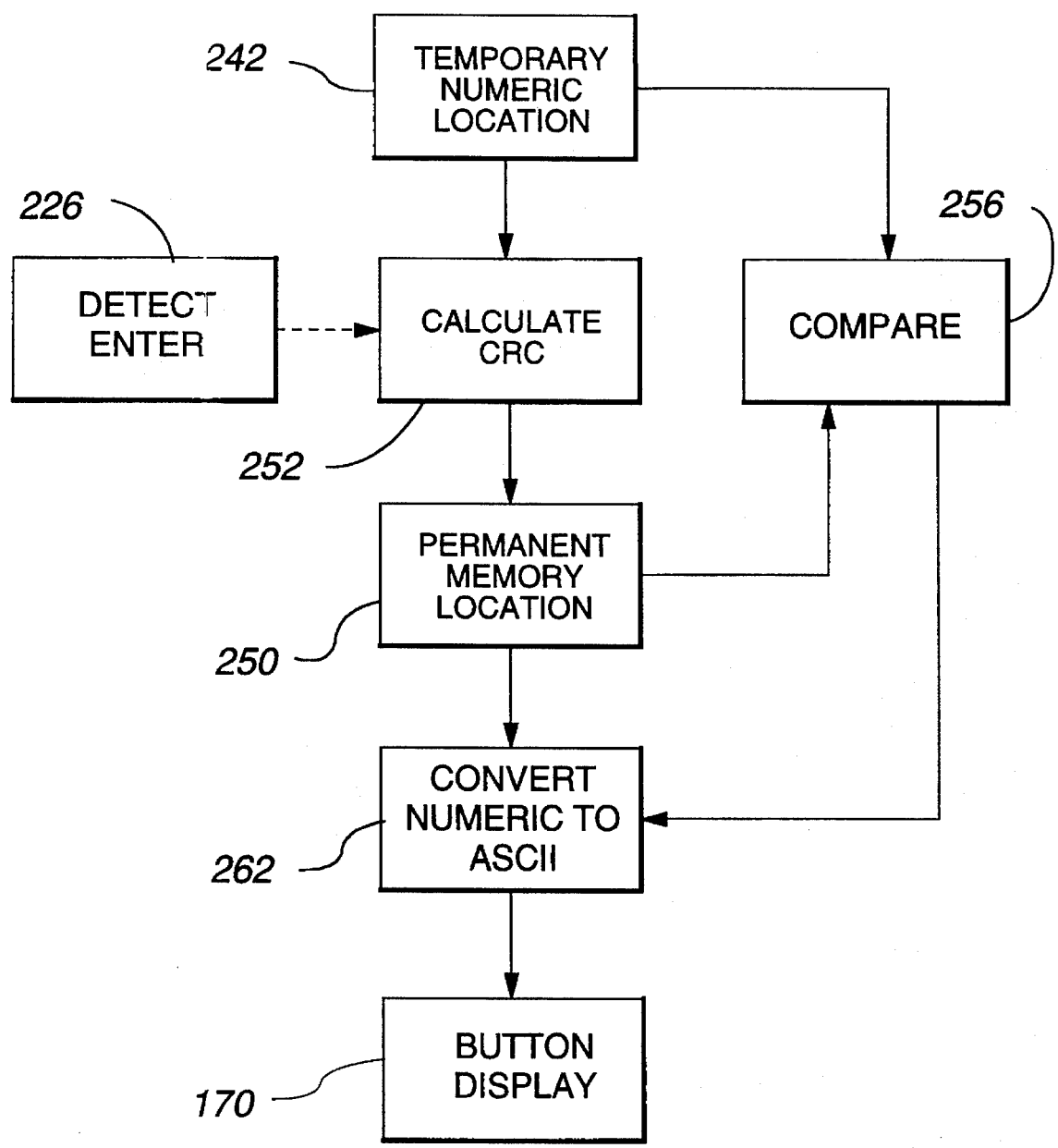
FIG. 11 is an illustration of some of the steps in The flow chart shown in FIG. 9B and the relationship of those steps with a permanent memory shown in FIG. 3.

Each time a numeric value is derived at step 238, all of the values which have previously been recorded in the cells 236a, 236b, 236c, . . . 236n are used in the ASCII-to-numeric conversion, as is shown in FIG. 10. In this manner, the value displayed at step 248 (FIG. 9A) constitutes a measure of the collective accuracy of each value previously and presently entered. Since the collective information of all of the previous values is used in the last ASCII to numeric conversion, rather than simply updating the information previously displayed with each new conversion, any mistake in the selected values is likely to be recognized by the operator.

Furthermore, the entry and conversion technique provides the operator with an effective indication of whether the stored information may have become corrupted. Should the operator receive the display of a value which the operator did not enter, or if a previously entered value suddenly changes with a subsequent entry, corruption of the entered information is suggested. A circumstance of a computational malfunction in the two conversions (ASCII to numeric, and numeric back to ASCII) might also be suggested. In either circumstance, the operator is alerted to a potential malfunction within the dialysis machine, and the operator should recognize that the machine should not the used for the dialysis treatment.

The use of the font table to display the values also provides a continuing indication of the functionality of the system. Preferably the font table is the only font table employed in the safety system for the display of information to the operator. By use of the single font table, the potential problems of corruptions of multiple font tables are avoided. Reference to a single font table for all displayed characters is more likely to reveal a malfunction within the system, since data displayed by use of the single font table will indicate corruption through the improper display of that data. The likelihood that the font table itself has become corrupted will be apparent if other information displayed to the operator is improper. These types visual cues provided through the display of information constitute a continuing integrity check of the functionality of the safety system microcontroller 122.

Further still, the display of the entered information also creates certain inherent protections against operator induced errors. The repetitive display of the information previously entered constitutes a requirement that the operator continually accept the previous values as well as the present values entered. Each subsequent step of entering additional values inherently causes the operator to re-evaluate the previous information presented on the display area 206 of the keypad 202 (FIG. 5). Consequently the entry process inherently creates a naturally-appearing requirement for reconsideration and re-validation of the previously entered information. However, this form of re-validation occurs inherently in conjunction with the natural process of entering each new value, not as an artificial and time-consuming requirement to specifically enter data twice or to look at data appearing in two different locations on the dialysis machine. Validation of the entered information appears transparent to the operator, but the integrity of the validation does not compromise safety or encourage inattentive or slack practices by the operator. Entered information is validated in a manner which appears natural and second-nature to the operator. The awkward, time-consuming and somewhat frustration-prone necessity to continually compare two different values displayed at different locations on a screen, or to enter values twice, is avoided.

Figure 7:
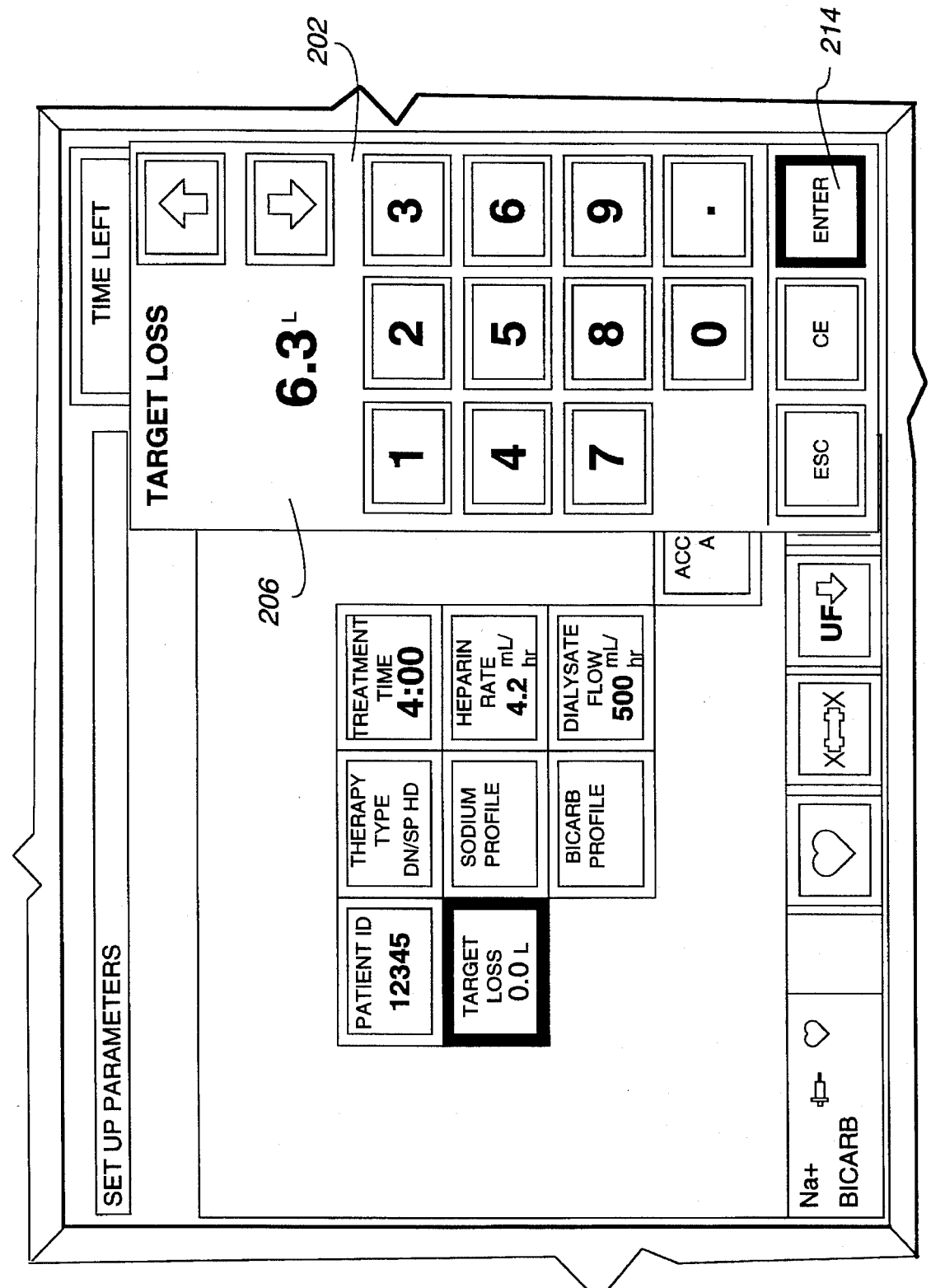

After all of the information has been entered in the manner shown and described in conjunction with FIG. 9A, the resulting end value is displayed in the display area 206 of the keypad 202, as is shown by the example of the value "6.3" in FIG. 7. The value thus derived is stored in the temporary ASCII array 234 (FIG. 3) and in the temporary numeric memory 242. Even though the desired value may be displayed correctly, this value will not be accepted for use by either the safety microcontroller 122 or the extracorporeal or hydraulics microcontrollers 112 and 118 of control system.

To make an entered value available for use by the control and safety system of the dialysis machine, the operator must select the enter button 214 as shown in FIG. 7. Selection of the enter button 214 initiates the program flow shown in FIG. 9B to assure that the information which has been validated by the operator will be recorded in a permanent memory segment 250 (FIG. 3) of the safety system memory 124. Once the value is recorded in the permanent memory segment 250, the control system microcontrollers 122 and 118 gain access to the information by reading the values in the permanent memory from the network 126. Touching the enter button causes the temporary ASCII memory array 236a, 236b, 236c, etc. to become available for reuse during the same process with the next selected information.

Detection of the enter button at step 226 causes the microcontroller 1.22 to calculate a cyclic redundancy check (CRC) value based on the information contained in the temporary memory location 242. The calculation of the CRC occurs at step 252 as shown in FIGS. 9B and A CRC is a value derived from the bit structure of the particular value contained in the temporary memory location 242, and the CRC is used to detect errors that may occur from corruption of the value occurring after the CRC has been calculated. Errors of this nature may sometimes arise from failures of memory or due to corruption occurring when information is transferred to or obtained from memory within the computer system. The CRC may be calculated by using any number of well known CRC calculation algorithms.

After calculation of the CRC at 252, the calculated CRC is associated with the numeric value from which it was calculated, and the numeric value and its corresponding CRC are stored in the permanent memory location 250 (FIG. 3), as shown at the step 254. The values stored in the permanent memory location 250 are in a form acceptable for use and transfer between the safety system and the control system microcontrollers of the dialysis machine. However before the numeric and CRC values are made available for use by the management system, a further validation of the values recorded in the permanent memory 250 is performed.

The numeric value stored in the temporary numeric memory location 242 is compared at step 256 to the numeric value stored in the permanent memory location 250. If the comparison at 256 reveals that the values in the two memory locations 242 and 250 are different, an error has occurred and the value stored in the permanent memory 250 is not reliable or consistent with the value which has previously been validated and accepted by operator action as represented by the value located in the temporary memory 242. In this circumstance, all previously entered values in the temporary memory locations 234 and 242 and in the permanent memory 250 are erased at step 258 and the program flow reverts back to step 224 (FIG. 9A). Erasing the values causes the operator to commence again the information entry and validation procedure shown in FIG. 9A.

Figure 8:
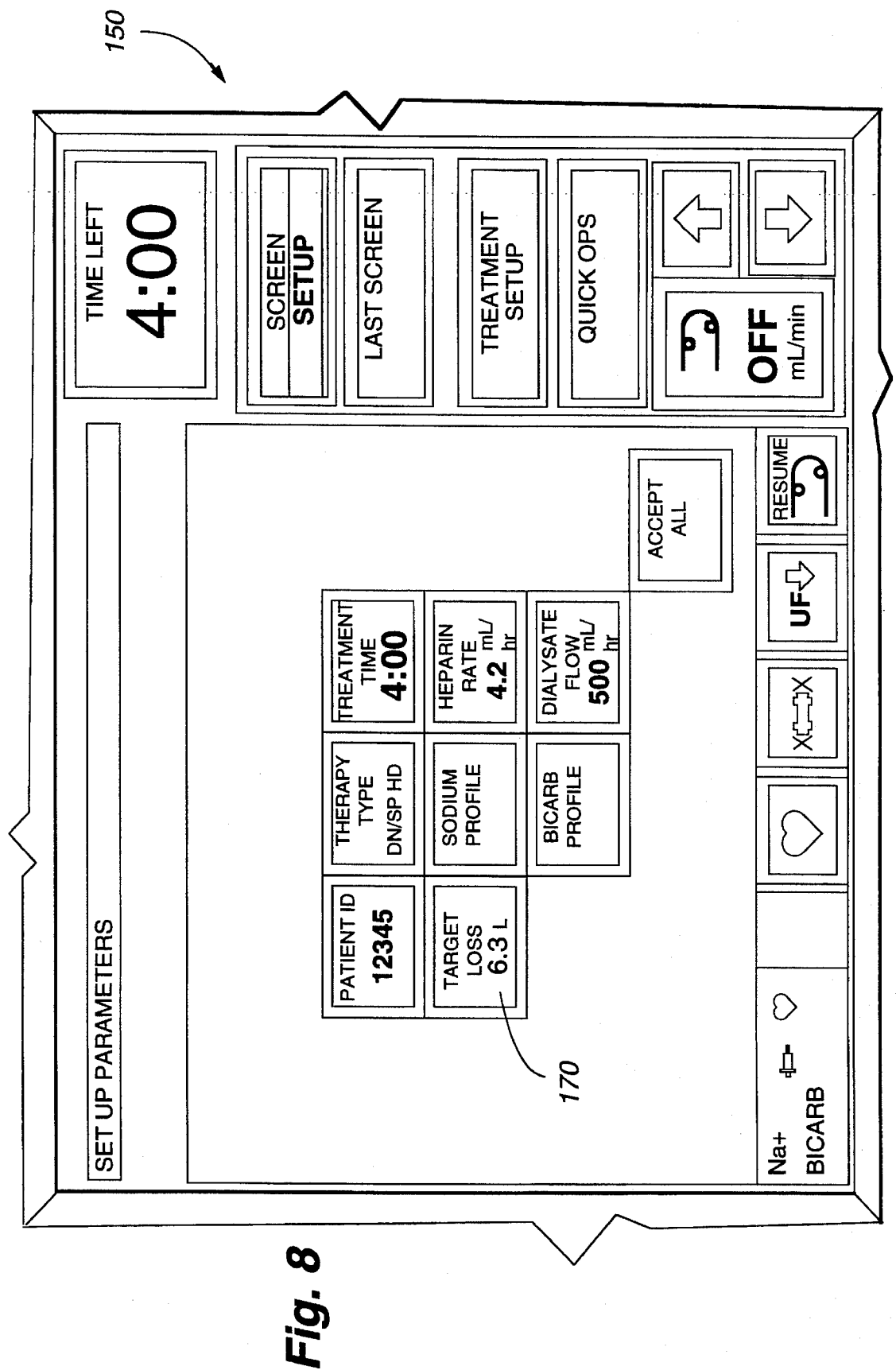

If the comparison performed at 256 reveals that the values in memory at 242 and 250 are equal, the keypad display 202 is erased from the display screen 150 by the step shown at 260 in FIG. 9B. The absence of the keypad 202 from the display screen is shown in FIG.8. Thereafter, the value in the permanent memory 250 is converted to an ASCII value, as shown at 262. Again, the font table 220 may be employed to make the conversion if it is not inherent in the program which establishes the numeric value.

The microcontroller 122 supplies the ASCII value derived from the conversion at step 262 to the video driver 238, as shown at step 264, and the signals from the video driver 138 are used by the CRT 132 to display the final value, as shown at step 266. The final value displayed at 266 is the same value which was accepted by the operator by touching the enter button 214 of the keypad 202. However, since the keypad 202 has been erased at step 260, the final value is displayed on the setup parameter button 170 (FIG. 8) which was initially selected at step 200 to initiate the information entry and validation technique of the present invention.

After acceptance of the value in the permanent memory as determined by the comparison at 256, the value in the permanent memory 250 is available to be transferred to and used by the management system extracorporeal and hydraulics microcontrollers 112 and 118, respectively. Transfer of the value to the microcontrollers 112 and 118 results in that value being stored in their memories 114 and 120, respectively, as is shown at step 268. The use of permanent memory 250 (FIG. 3) for storing the values used by the safety microcontroller 122 assures that those values will be available to the safety system after start-up following a power loss to the dialysis machine.

The information entry validation technique of the present invention achieves a number of significant improvements for the operators of dialysis machines. The information entered by the operator is inherently validated in a convenient and time-conserving manner, as a natural adjunct to the entry of information itself. The entire value displayed is re-presented to the operator with each subsequent entry. Each subsequent entry therefore confirms all of the previous entries and presents the result to the operator. Should the operator have failed to recognize an error occurring from a previous entry, each subsequent entry of information presents another opportunity for the operator to recognize a previous error. Furthermore, the final entered value must be accepted by the operator by selecting the enter button to re-affirm the final acceptance of the entered information. The removal of the keypad upon selection of the enter button and the resulting display of the final value in the parameter setup button requires the operator to again confirm the value. These procedures for presenting information to the operator for confirmation appear to the operator as natural sequential events, not the redundant and repetitious double-entry and double-display confirmation operations which are typical in the prior art. As a result, the operator is less likely to make mistakes arising from boredom, from inattention inherent in repeating redundant actions, or from tension and tedium caused by the typical double-entry requirements of prior art dialysis machines. Furthermore, these significant operator advantages are obtained without compromising safety, and while meeting the safety and governmental standards which apply to dialysis machines. Further still, the present invention allows the operator to enter information more rapidly while still achieving these significant conveniences.

The information entry validation technique of the present invention also offers significant improvements in the functional operations associated with the information entry and validation. The use of two separate conversions, such as ASCII to floating point numeric, serves as a double-check on the functionality of the machine. Furthermore the use of a single font table by which to achieve the conversions eliminates the possibility that errors could occur in one font table that were not present in another font table. The use of multiple memory locations to store values obtained from the two conversions, and to store the permanent value substantially reduces the possibility that an error in the memory might allow a corrupted value to be used by the dialysis machine. The comparison of the temporary and permanent values before the final value is accepted for use by the control and safety systems of the machine constitutes a further check on the validity of the accepted information. Many other significant improvements will be recognized after the present invention is fully comprehended and appreciated.

A presently preferred embodiment of the invention and many of its improvements have been described with a degree of particularity. This description is a preferred example for implementing the invention, and is not necessarily intended to limit the scope of the invention which is defined by the following claims.

The invention claimed is:

1. A dialysis machine having an operator/machine interface by which an operator enters control and safety information for use by the dialysis machine, said dialysis machine comprising:

an information entry device;

a display device; and a safety system connected to the information entry device and the display device, the safety system including means for firstly converting information entered from the entry device into a first form using a first conversion relationship, and thereafter for secondly converting the information in the first farm to a second form using a second conversion relationship which is different from the first conversion relationship, and thereafter for thirdly converting the information from the second ram back to the first form using the first conversion relationship;

the safety system farther including menu for controlling the display device to display the information in the first form which resulted from the third conversion, and means for registering acceptance or rejection information supplied by the operator at the entry device to accept or reject the displayed information which resulted from the third conversation.

2. A dialysis machine as defined in claim 1 wherein the first relationship is an ASCII conversion relationship.

3. A dialysis machine as defined in claim 2 further comprising a single font table which establishes the form of all the information displayed.

4. A dialysis machine as defined in claim 2 wherein the second relationship is a numeric conversion relationship.

5. A dialysis machine as defined in claim 4 wherein the numeric conversion relationship is a floating point numeric conversion relationship.

6. A dialysis machine as defined in claim 1 wherein:

the safety system includes a memory flaring a first location and a second location;

the safety system includes means for storing the information in the first form in the first memory location and for storing the information in the second form in the second memory location; and the entered information includes a plurality of individual values entered sequentially, each value is converted as information in the manner aforesaid end displayed before the next value is entered, the first memory location includes a plurality of memory cells, each value is stored in a separate memory cell after conversion of the value into the first form, and the values stored in all of the memory cells are collectively employed in the conversion into the second form.

7. A dialysis machine as defined in claim 6 wherein the information in the second form is obtained from the second memory location prior to the third conversion.

8. A dialysis machine as defined in claim 6 wherein:

the memory of the safety system further includes a third memory location, the storing means of the safety system also stores the information in the second memory location in the third memory location, the safety system further includes means for comparing the information in the second and third memory locations, and the safety system uses the information in the second form obtained from the second memory location in the third conversion to create the displayed information.

9. A dialysis machine as defined in claim 6 wherein:

the safety system updates the displayed information to include each value when entered;

the means for registering acceptance or rejection information with respect to each of the sequential values entered; and the information in the second memory location is stored in the third memory location and the information in the second and third memory locations are compared after the acceptance of a plurality of values is registered.

10. A dialysis machine as defined in claim 9 wherein:

the safety system further includes means for calculating an error detecting code based on the information stored in the second memory location, and the storing means of the safety system stores the error detecting code in the third memory location along with the information stored in the third memory location.

11. A dialysis machine as defined in claim 9 further including:

a control system to control operations of the machine during dialysis treatments, and wherein:

the information in the third memory location is available for use by the control system after acceptance of the information is registered.

12. A dialysis machine as defined claim 9 wherein the information entry device includes a touch screen, the display device has a viewing surface, the touch screen overlays the viewing surface, the information entry device further includes a keypad displayed in an area of the viewing surface behind the touch screen, information tram the second memory location is displayed in an area of the keypad display before acceptance or the information is registered, and the information from the third memory location is displayed at a location on the viewing surface other than at the area of the keypad after acceptance of the information is registered.

13. A dialysis machine as defined claim 1 wherein the information entry device includes a touch screen, the display device has a viewing surface, the touch screen overlays the viewing surface, and the information entry device further includes a keypad displayed in an area of the viewing surface behind the touch screen for entry of the information.

14. A dialysis machine having an operator/machine interface by which an operator receives information describing operation and safety conditions of the machine and characteristics for treatment of a patient by the machine, said dialysis machine comprising:

display device operable for displaying internal information from the machine to the operator in response to the application of display signals to the display; and a safety system including:

a memory within which a font table is recorded, and means for creating the display signals by correlating the internal information with the font table to derive the display signals, the display signal creating means utilizing only the font table for correlating all of the internal information into the display signals.

15. A dialysis machine having an operator/machine interface by which an operator enters control and safety information for the machine, said dialysis machine comprising:

information entry devices;

a display device; and a control operative system for controlling the operation of the machine and including a control system memory within which to record operating information to be used for operating the machine;

a safety system connected to the information entry device, the display device and the control system, the safety system including:

a safety system memory having a first memory location and a second memory location, means for converting information entered from the entry device into a first form and for storing the information in the first form in the first memory location, means for copying the information stored in the first memory location into the second memory location, means for comparing the information stored in the first and second memory locations, and means for erasing the information in the first memory location and maintaining the information in the second memory location and for copying the information from the second memory location into the control system memory upon the comparison of the information in the first and second memory locations indicating equality.

16. A dialysis machine as defined in claim 15 wherein the safety system further includes:

means for calculating an error detecting code based on the information stored in the first memory location, and means for storing the error detecting code in the second memory location along with the information stored in the second memory location.

17. A dialysis machine as defined in claim 15 wherein the safety system further includes:

means for displaying the information stored in the first memory location;

means for registering acceptance of the information displayed and obtained from the first memory location, and the comparing means and the erasing and copying means becoming operative to perform their respective recited functions upon registration of acceptance of the information displayed and obtained from the first memory location.

18. A method of validating control and safety information entered into and to be used by a dialysis machine during dialysis treatment, comprising the steps of:

entering information using an information entry device of the machine;

firstly converting information entered from the entry device into a first form using a first conversion relationship;

secondly converting the information in the first form to a second form using a second conversion relationship which Is different front the first conversion relationship;

thirdly converting the information from the second form back to the first form using the first conversion relationship;

displaying the information in the first form which resulted from the third conversion; and requiring an operator of the machine to accept or reject the information displayed to continue operation of the machine.

19. A method as defined in defined in claim 18 further comprising the steps of:

using an ASCII conversion as the first conversion relationship;

using a numeric conversion as the second conversion relationship; and using the ASCII conversion to establish the form of the information displayed.

20. A method as defined in claim 18 further comprising the steps of:

providing a first memory location in which to store information;

formulating the entered information from a plurality of values entered sequentially, separately converting and displaying each value before the next value is entered, dividing the first memory location into a plurality of memory cells, storing each value entered in the first form in a separate memory cell, and collectively using all of the values stored in the memory cells in the conversion of the information into the second form.

21. A method as defined in claim 18 further comprising the steps of:

providing first, second and third memory locations in which to store information, storing the first form of information in the first memory location, storing the second form of information in the second memory location, obtaining the second form of information from the second memory location for use in the third conversion, displaying the information resulting from the third conversion, formulating the entered information from a plurality of values entered sequentially, separately converting and displaying each value before the next value is entered, displaying each new value when the new value is entered, requiring an operator of the machine to accept or reject the each new value displayed to continue operation of the machine, copying the information stored in the second memory location to the third memory location after the operator has accepted a last one of a group of new values entered, and comparing the information stored in the second and third memory locations after the operator has accepted the last one of the group of new values entered.

22. A method of displaying internal information train a dialysis machine which describes operational and safety conditions of the machine and characteristics of treatment of a patient by the machine while simultaneously confirming proper internal operation of at least a part of the dialysis machine, comprising the steps of:

displaying internal information from the machine, recording a font table in a memory within the machine, deriving characters of the displayed internal information by correlating the internal information with the font table, and using only the font table for all correlations of internal information with characters displayed.

23. A method of entering control and safety information into a dialysis machine for use in a control system and in a safety system of the dialysis machine during a dialysis treatment of a patient using the machine, comprising the steps of:

recording control information in a memory of the control system to control the dialysis machine during treatments, recording safety information in a memory of the safety system to monitor the operation of the dialysis machine and the condition of the patient during treatment, dividing the memory of the safety system into a first location and a second location, entering treatment information, converting the treatment information entered into a predetermined form and storing the converted information in the predetermined form in the first memory location, copying the information stored in the first memory location into the second memory location, and comparing the information in the first and second memory locations, and upon the information in the first and second memory locations indicating equality, erasing the information in the first memory location, and maintaining the information in the second memory location, and copying the information from the second memory location into the control system memory.

24. A method as defined in claim 23 further comprising the steps of:

displaying the information in the first memory location;

requiring an operator of the machine to accept the information displayed to continue, performing the steps of comparing the information, erasing the information from the first location, and copying the information into the control system memory after the operator accepts the information.

25. A method as defined in claim 24 further comprising the steps of:

calculating an error detecting code from the information stored in the second memory location, and storing the error detecting code in the second memory location, and performing the steps of calculating and storing the error detecting code after the operator accepts the information.

26. A dialysis machine having an operator/machine interface by which an operator enters control and safety information for use by the dialysis machine, said dialysis machine comprising:

an information entry device;

a display device: and a safety system operatively connected to the entry device and the display device, the safety system including a memory having first, second and third memory locations, the safety system being operative to:

convert information entered from the entry device into a first form and store the information in the first form in the first memory location, convert the information in the first form to equivalent information in a second form and store the information in second form in both the second and third memory locations, compare the information in the second and third memory locations for equivalency, convert the information in the second form obtained from the second memory location to a third form, and control the display device to display the information in the third form.

27. A dialysis machine as defined in claim 26 wherein the entered information includes a plurality of individual values entered sequentially, and the safety system is further operative to:

convert each value as information in the manner aforesaid;

display each value before the next value is displayed;

update the display to include each value which is entered before the next value is displayed;

register acceptance of each value displayed; and compare the values of the information in the second and third memory locations after the acceptance of a plurality of values is registered.

28. A dialysis machine as defined in claim 27 wherein the safety system is further operative to:

calculate an error detecting code based on the information stored in the second memory location, and store the error detecting code in the third memory location along with the information in the second form stored in the third memory location.

29. A dialysis machine as defined in claim 28 further including:

a control system to control operation of the machine during dialysis treatments, and wherein:

the control system operative to use the information in the third memory location to control the machine.

30. A dialysis machine as defined in claim 27 wherein:

the information entry device includes a touch screen;

the display device has a viewing surface;

the touch screen overlays the viewing surface;

the information entry device further includes a keypad display on the viewing surface behind the touch screen;

information from the second memory location is displayed in the keypad display before acceptance of the values is registered; and the value from the second memory location is displayed on the viewing surface at a location other than the keypad display after acceptance of the values is registered.

31. A dialysis machine as defined in claim 26 wherein the safety system is further operative to:

calculate an error detecting code based on the information stored in the second memory location, and store the error detecting coda in the third memory location along with the information in the second form stored in the third memory location.

32. A dialysis machine as defined in claim 26 further including:

a control system to control operation of the machine during dialysis treatments, the control system functioning separately from the safety system, and the control system being operative to use the information in the third memory location to perform control operations.

33. A dialysis machine having an operator/machine interface by which an operator enters control and safety information for the machine, said dialysis machine comprising:

information entry device;

a display device; and a control system for controlling the operation of the machine and including a control system memory within which to record operating information to be used for controlling the machine;

a safety system connected to tho entry device and the display device and the control system, the safety system including a safety system memory having a first location and a second location, the safety system being operative to:

convert information entered from the entry device into a first form and store the information in the first form in the first memory location, copy the information stored in the first memory location into the second memory location, calculate an error detecting code based on the information stored it the first memory location, store the error detecting code in the second memory location along with the information stored in the second memory location, and copy the information and the error detecting code stored in the second memory location into the control system memory.

34. A dialysis machine as defined in claim 33 wherein the safety system is further operative to:

compare the information in the first and second memory locations, and upon the comparison of the information in the first and second memory locations indicating equality, erase the information in the first memory location, and maintain the value in the second memory location.

35. A dialysis machine defined in claim 34 wherein the safety system is further operative to:

control the display device to display the information stored in the first memory location;

register acceptance of the displayed information stored in the first memory location, and upon acceptance of the displayed information stored in the first memory location execute the compare, erase and copy operations.

36. A dialysis machine having an operator/machine interface by which an operator enters control and safety information for use by the dialysis machine, said dialysis machine comprising:

an information entry device;

a display device; and a safety system operatively connected to the entry device and the display device, the safety system operative to:

convert information entered from the entry device into a first form using a first conversion relationship, and thereafter convert the information in the first form to a second equivalent form using a second conversion relationship which is different from the first conversion relationship, and thereafter convert the information from the second form back to the first form using the first conversion relationship; and thereafter control the display device to display the information in the first form which resulted from the third conversion.

37. A dialysis machine as defined in claim 36 wherein the first relationship is an ASCII conversion relationship.

38. A dialysis machine as defined in claim 37 wherein the second relationship is a numeric conversion relationship.

39. A dialysis machine as defined in claim 38 wherein the numeric conversion relationship is a floating point numeric conversion relationship.

40. A dialysis machine as defined in claim 36 further comprising a single font table which establishes the form of all the information displayed.

41. A dialysis machine having an operator/machine interface by which an operator receives information describing the operation and safety conditions of the machine and the characteristics of the treatment, said dialysis machine comprising:

an intonation entry device by which to enter information describing operation and safety conditions of the machine;

a display device by which to display information from the machine, the display device creating displays of information for the operator in response to the application of display signals applied to the display device; and a safety system connected to the entry device and the display device, the safety system including a memory in which a font table is recorded, the safety system being operative to:

receive entered information from the entry device;

generate internal information describing the operative conditions or the machine;

correlate all entered and internal information to be displayed to the font table;

create display signals corresponding to the entered and internal information frost the correlation to the font table; and apply the created display signals to the display device to display the entered and internal information.

42. A dialysis machine having an operator/machine interface by which an operator enters control and safety information for the machine, said dialysis machine comprising:

an information entry device;

a display devices; and a control system for controlling the operation of the machine and including a control system memory within which to record machine operating information;

a safety system for monitoring the proper operation of the machine and the condition of a patient undergoing dialysis, the safety system connected to the information entry device and the display device, the safety system having a first and second memory locations, the safety system being operative to:

convert information entered from the entry device into a first form, store the information in the first form in the first memory location, convert the information in the first form to a second equivalent form, store the information in the second form in the second memory location, compare the information in the first and second memory locations, and upon the comparison indicating equality erase the information in the first memory location, and maintain the information in the second memory location, and copy the information from the second memory location to the control system memory for use by the control system.

43. A dialysis machine as defined in claim 42 wherein the safety system is further operative to:

calculate an error detecting code based on the information stored in the second memory location, and prior to copying the information from the second memory location to the control system memory store the error detecting code in the second memory location.

44. A dialysis machine as defined in claim 42 wherein the safety system is further operative to:

control the display device to display the information in the second memory location;

register acceptance of the information displayed was obtained from the second memory location, and perform the compare, erase and copy operations upon registration of acceptance of the information displayed.

* * * * *